(12) United States Patent
Murray

(10) Patent No.: US 11,445,275 B2
(45) Date of Patent: Sep. 13, 2022

(54) SOIL AND ENVIRONMENT SENSOR AND METHOD OF USE

(71) Applicant: Michael Murray, Lexington, MA (US)

(72) Inventor: Michael Murray, Lexington, MA (US)

(*) Notice: Subject to any disclaimer, the term of this patent is extended or adjusted under 35 U.S.C. 154(b) by 0 days.

(21) Appl. No.: 17/176,087

(22) Filed: Feb. 15, 2021

(65) Prior Publication Data

US 2021/0258661 A1     Aug. 19, 2021

Related U.S. Application Data

(60) Provisional application No. 62/977,197, filed on Feb. 15, 2020.

(51) Int. Cl.
*G01N 33/24*     (2006.01)
*H04Q 9/02*     (2006.01)

(52) U.S. Cl.
CPC .............. *H04Q 9/02* (2013.01); *G01N 33/246* (2013.01); *H04Q 2209/40* (2013.01); *H04Q 2209/88* (2013.01)

(58) Field of Classification Search
None
See application file for complete search history.

(56) References Cited

U.S. PATENT DOCUMENTS

| 5,418,466 A * | 5/1995 | Watson ................ G01N 27/025 324/668 |
| 10,499,573 B1 * | 12/2019 | Paulsen .................. A01B 63/02 |
| 2009/0219037 A1 * | 9/2009 | Campbell ............ G01N 33/246 324/664 |
| 2016/0183484 A1 * | 6/2016 | Richings, Sr. ....... A01G 25/167 239/11 |
| 2017/0254766 A1 * | 9/2017 | Bermudez Rodriguez .................. G01N 27/048 |
| 2020/0132658 A1 * | 4/2020 | Koch ................... A01C 21/007 |

FOREIGN PATENT DOCUMENTS

| WO | WO-2007002994 A1 * | 1/2007 | .......... G01N 33/246 |
| WO | WO-2019070942 A1 * | 4/2019 | .......... G01N 33/246 |
| WO | WO-2019245367 A1 * | 12/2019 | .......... G01N 27/048 |

\* cited by examiner

*Primary Examiner* — Curtis A Kuntz
*Assistant Examiner* — Jerold B Murphy
(74) *Attorney, Agent, or Firm* — Andrew Morabito

(57) ABSTRACT

The present invention is a sensor device comprising: a housing; a processing unit assembly disposed within the housing, wherein the processing unit comprising a high frequency oscillator, a first voltage meter, a low frequency oscillator, a second voltage meter; a probe having a predetermined shape and profile attached to the processing unit and extending from the housing a predetermined distance; and a first sensing unit integrated into the probe and in electrical communication with the high frequency oscillator and the first voltage meter; a second sensing unit integrated into the probe relative to the first sensing unit and in electrical communication with the low frequency oscillator and the second voltage meter.

19 Claims, 9 Drawing Sheets

SOIL AND ENVIRONMENT SENSOR AND METHOD OF USE

CROSS-REFERENCE TO RELATED APPLICATIONS

This application claims the benefit of priority under 35 USC 120 of U.S. application No. 62/977,197 filed Feb. 15, 2020. The disclosure of the prior applications is considered part of (and is incorporated by reference in) the disclosure of this application.

BACKGROUND

This disclosure relates generally to a sensor, and particularly to a sensor and a method of operation of the sensor for monitoring soil conditions.

The monitoring of the moisture of soil for the purpose of optimizing the growth of crops has become increasingly important today, particularly in the environment of large, corporate farming operations. There are two common practices associated with the installation of soil moisture probes in the soil. The most prevalent method involves the installation of a soil monitoring probe in the ground once the plant emerges after planting (actually a series of probes to cover an entire planted field). Each probe is then connected to a telemetry system that provides power and receives the measured data from the probe. The telemetry will regularly upload the received data to a central database using cellular or other wireless technology.

In conventional control system, the primary means for halting an automatic watering cycle when certain environmental event occurs is by an operator manually suspending the cycle at the irrigation controller. In most situations this proves to be an ineffective means of conserving resources due to the inconsistent and inefficient methods followed by the operator. In fact, quite often the operator ignores the need to suspend the watering cycle altogether, and in some cases neglects to resume the watering cycle when required, leading to both over-watered and under-watered landscaping.

It is because of this unreliable and inconvenient manual method that environmental sensors were developed that allow for an automatic interruption of the controller due to an environmental condition. One of the major drawbacks of the conventional environmental sensors is the extensive installation time and difficult methods required for a proper installation.

A less common practice is to install the probe(s) in the soil and then trench the connecting cable to the perimeter of the field (typically about 100 meters away). This will allow the probe to reside in the field continuously for several years, providing data to the grower over the entire year. There are several drawbacks with the trenching method. First, it is a cumbersome and expensive exercise to trench the cable (to each probe). Second, there are several cases where normal field operations will result in one or more of the cables being severed, thereby breaking the connection to the probe.

What is needed is a system and method that permits the probe to reside continuously in the field without the need for expensive trenching, and without the risk of damage to the equipment due to normal field operations. It is believed that a wireless probe transmission system that is buried in close proximity to each probe, is the solution to this problem.

The operator thus has the task of monitoring and controlling a variety of system parameters to achieve the best conditions for the specific plants in the installation. This can be time consuming. A failure to properly control the parameters may result in plant harm and financial loss. Additionally, if a component failure occurs while the operator is not on site, it may be detected too late to prevent harm. Component failures such as leaks, failed pumps, faulty temperature control devices or faulty lamps can occur at any time.

Often, it is financially advantageous to ensure the plants are growing at the fastest rate possible using the least number of resources. This often requires detailed analysis of present and historical data, looking for trends between nutrient and environmental conditions and plant response. This requires keeping accurate measurements of measured conditions and a method of recording plant growth and behavior, typically over the course of one or more growing seasons. Conventionally this is done by keeping records by hand, and requires additional time and effort, with the possibility of mistakes.

A soil moisture sensor is usually installed in the ground by boring of a precisely sized hole, placing the sensor at the appropriate depth to measure the soil properties in the root zone, placing a slurry of water and soil in the hole to assure that the sensor has good contact with the soil and try to restore the soil in the hole to its previous condition as much as possible so that the sensor provides readings that correctly reflect the state of the soil. If the soil is not restored properly, water and fertilizer can drain down along the hole to the sensor and corrupt the sensor readings.

It is desired for a soil sensor that is easy to install, collects accurate data, and provides wireless transmission of the data to central location.

SUMMARY

In a first embodiment the present invention is a sensor device comprising: a housing; a processing unit assembly disposed within the housing; a probe connected to the processing unit and substantially exposed; at least one sensing structure integrated into the probe and in electrical communication with the processing unit, wherein the at least one sensing structure provide information related to the moisture and salinity of soil, and the information is calculated by the processing unit based on data collected from the at least one sensing structures; and a signal generator in electrical communication with the processing unit and the at least one sensing structure.

In a second embodiment the present invention is a sensor device comprising: a housing; a processing unit assembly disposed within the housing, wherein the processing unit comprising a high frequency oscillator, a first voltage meter, a low frequency oscillator, a second voltage meter; a probe having a predetermined shape and profile attached to the processing unit and extending from the housing a predetermined distance; and a first sensing unit integrated into the probe and in electrical communication with the high frequency oscillator and the first voltage meter; a second sensing unit integrated into the probe relative to the first sensing unit and in electrical communication with the low frequency oscillator and the second voltage meter.

In a third embodiment the present invention is a sensor device comprising: a housing; a control module contained within the housing; a probe extending from the housing; and first sensing units integrated into the probe and in electrical communication with the control module; and a second sensing unit integrated into the probe and in electrical communication with the control module; wherein the control module is able to measure the impedance of the first and second sensing units to calculate a moisture and salinity value.

BRIEF DESCRIPTION OF THE DRAWINGS

Referring now to the drawings in which like reference numbers represent corresponding parts throughout.

DETAILED DESCRIPTION

Figure 1:
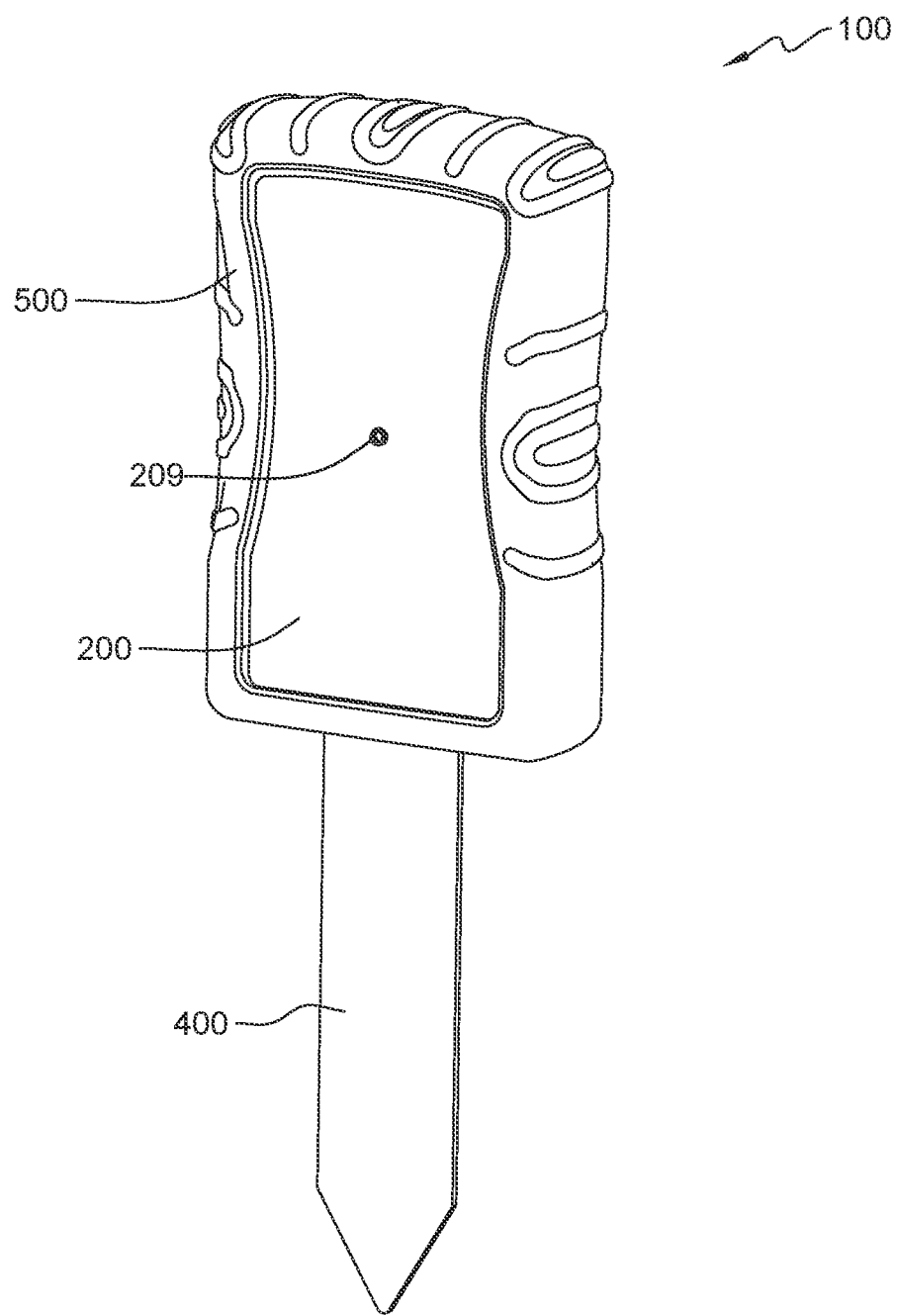
FIG. 1 depicts a perspective view of a soil sensor front side, according to an embodiment of the present invention.
Figure 2:
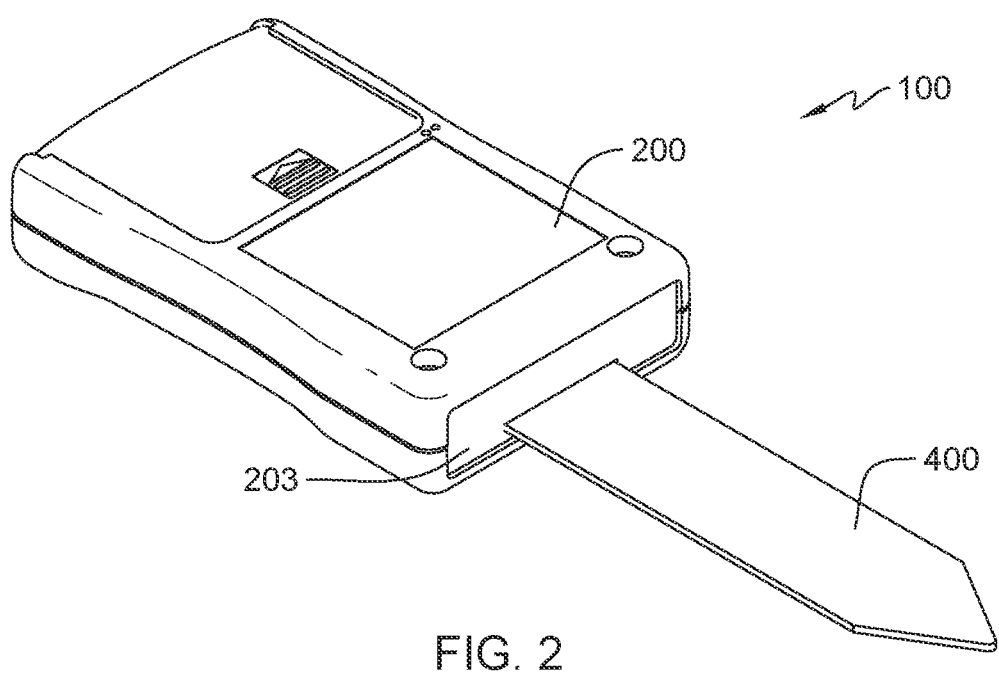
FIG. 2 depicts a perspective view of the soil sensor rear side, according to an embodiment of the present invention.

The present invention provides a device, a system, and a method of operation for monitoring soil properties and conditions to assist those who manage and maintain the crops accurate and current data to assist them in the watering and fertilization of the soil based on the specific plant or crops needs.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

FIGS. 1-5 depicts various views of a soil sensor 100, according to an embodiment of the present invention. The soil sensor is comprised of a housing 200, a circuit board 300, and a probe 400, and a cover 500. The housing 200 encapsulates the circuit board 300 and a portion of the probe 400. The probe 400 is in physical and electrical communication with the circuit board 300. In the depicted embodiments, the circuit board 300 and the probe 400 are a unitary component. In additional embodiments, the probe 400 may be detachable or can be disconnected from the circuit board 300. The cover 500 is a rubber or protective cover designed to protect the housing 200 and the internals from impact.

The housing 200 is comprised of a firm shell which is fitted around the circuit board 300 to form a substantially watertight seal around the circuit board 300. The housing 200 in the depicted embodiment is comprised of a back plate 201, a front plate 202 and a lower plate 203 and a battery cover 204. In the depicted embodiment, a battery 205 (or batteries) are stored within the housing 200 and are used to power the device and are replaceable. In the present embodiment a 9 Volt battery is used. In some embodiments, a solar panel or device capable of collecting renewable energy (e.g., solar, wind, etc.) may be incorporated into the housing 200 and a rechargeable battery (lithium cell batter) may be used in replace of the replaceable batteries. The front plate 202 and the back plate 201 are secured together through fasteners inserted through openings 207A and secured into apertures 207B. The circuit board 300 is secured in place with fasteners inserted through apertures 308 and secured into apertures 208 or 309 depending on which plate the circuit is secured to. An outer rubber, silicone, or the like cover 205 is secured around the housing 200 for additional protection as shown in the depicted embodiments. Lower plate 203 is fitted between the front and back plates through grooves 212 and 213. The lower plate 203 has a slot 206 which is sized to fit the probe 400. The lower plate 203 creates a substantially watertight seal around the front plate 202, the back plate 201, and the probe 400.

Figure 3:
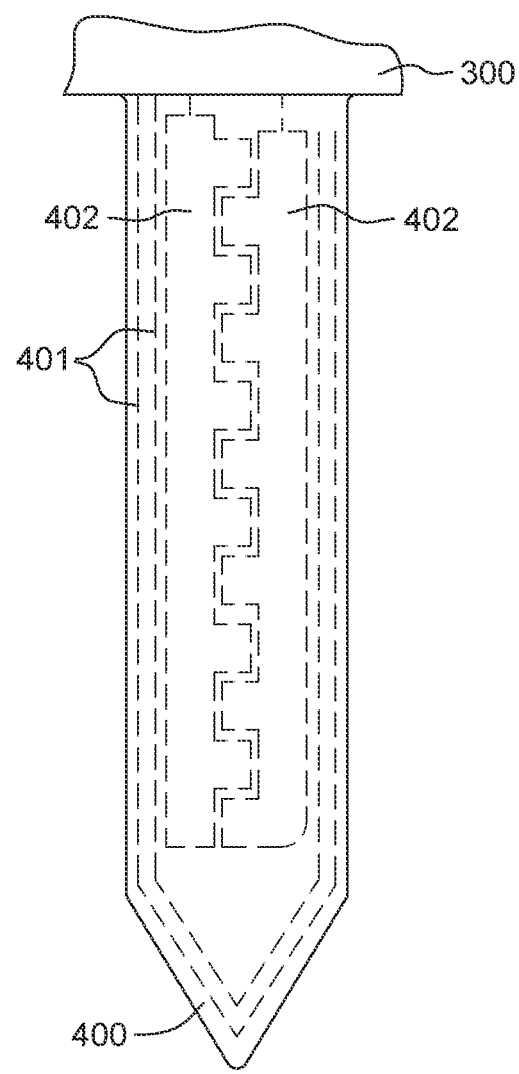
FIG. 3 depicts a front view of a probe and circuit board, according to an embodiment of the present invention.

FIG. 3 depicts a front view of the probe 400 and a portion of the circuit board 300, according to an embodiment of the present invention. The probe 400 is designed house the capacitive sensing nodes 401 and 402 which are used to collect voltage readings, which are then used to calculate various properties from the soil, such as moisture, fertilizer concentration, and the salt concentration or salinity of the soil. In the present embodiment, the probe 400 has a stake like design and is substantially flat, and there is a single probe 400. In additional embodiments, more than one probe 400 may be present. The probe 400, in the present embodiment is similar in structure to a manufactured circuit board where a series of layers of resin are formed around a copper substrate. In the present embodiment, the probe 400 is comprised of a top solder mask layer made from epoxy, a top foil layer made from copper, a prepreg top layer made from FR4 material, an inner top layer of copper, a core of FR4, an inner lower layer of copper, a Prepreg bottom layer of FR4, a bottom copper layer, and a bottom solder mask of epoxy. an exterior top layer, an upper inner layer, a lower inner layer, and exterior bottom layer. The thickness and the shape of the probe 400 are based on the capacitive sensing nodes design. This is to say that other shapes can be used provided the capacitive sensing nodes (401 and 402) are able to accurately collect the data needs. The material, which is used to encase the capacitive sensing nodes 401 and 402, is a material that will provide little to no interference with the capacitive sensing nodes 401 and 402 ability to collect the data from the soil.

In one embodiment, the probe 400 and the circuit board 300 are a unitary component. As shown the probe 400 has two capacitive sensing nodes 401 which run along the edge of the probe 400 and a set of capacitive sensing nodes 402 are positioned towards a center line of the probe 400. The capacitive sensing nodes 402 are shaped to have substantially mating edges that are spaced a predetermined distance apart to keep the two capacitive sensing nodes 402 from coming in contact with one another. In the present embodiment, the capacitive sensing nodes 402 have six "teeth" each and have a comb like design. The thickness of the teeth, the length of the teeth, and the gap between the teeth and between the capacitive sensing nodes 401 and 402 are predetermined and based on the intended operation of the device. In additional embodiments, the number of teeth may be modified or the profile of the capacitive sensing nodes 402 may be altered. If the number of teeth is adjusted or the surface area of the capacitive sensing nodes 402 is modified the accuracy of the data may be affected, and thus the capacitive sensing nodes 402. The number of the capacitive sensing nodes 401 and 402, the positioning of the capacitive sensing nodes 401 and 402, and the size of the capacitive sensing nodes 401 and 402 is all adjustable based on the probe 400 design and the soil type.

The capacitive sensing nodes 401 and the capacitive sensing nodes 402 use specific frequencies to measure the moisture and salinity of the soil. Through the use of frequency oscillators, the capacitive sensing nodes 401 are able to measure the moisture of the soil and the capacitive sensing nodes 402 are able to measure the salinity of the soil. The soil moisture circuit includes a high frequency oscillator, a voltage meter, and a capacitor. The soil salinity circuit includes a low frequency oscillator, a voltage meter, and a resistor of a known value. The capacitive sensing nodes 401 operate at a frequency between 7 Mhz and 9 Mhz and the capacitive sensing nodes 402 operate at a frequency between 400 Khz and 600 Khz. The frequency of the capacitive sensing node 401 and the capacitive sensing node 402 is based on the design of the probe 400 and the physical features of the capacitive sensing nodes 401 and 402. the surface area, thickness of the capacitive sensing nodes 401 and 402, and the frequency of the capacitive sensing nodes 401 and 402. Given the wide variety of soils, the capacitive sensing node 401 and the capacitive sensing node 402 may be sized based on a desired soil type, or a desired reading of the moisture and salinity of the soil.

Figure 3B:
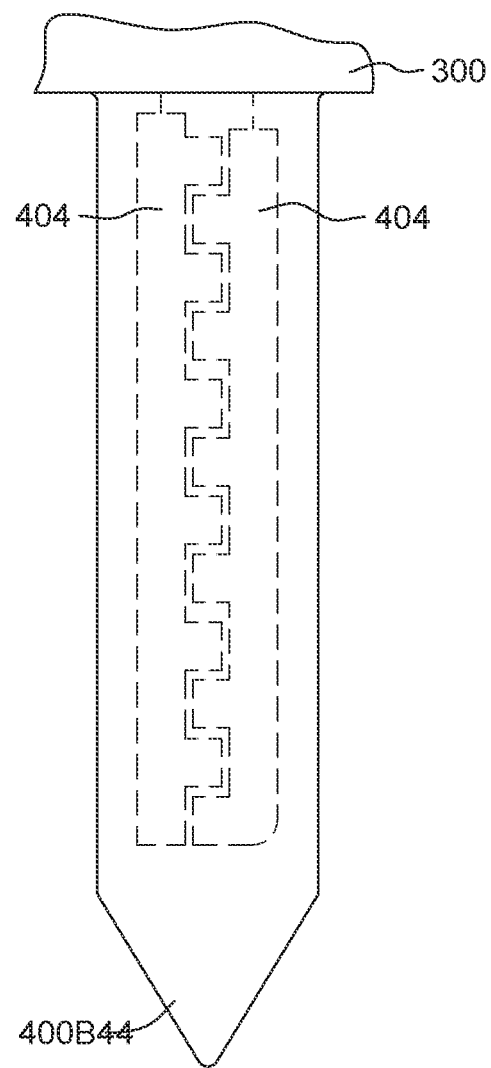
FIG. 3B depicts a front view of a probe and circuit board, according to an embodiment of the present invention.
Figure 4:
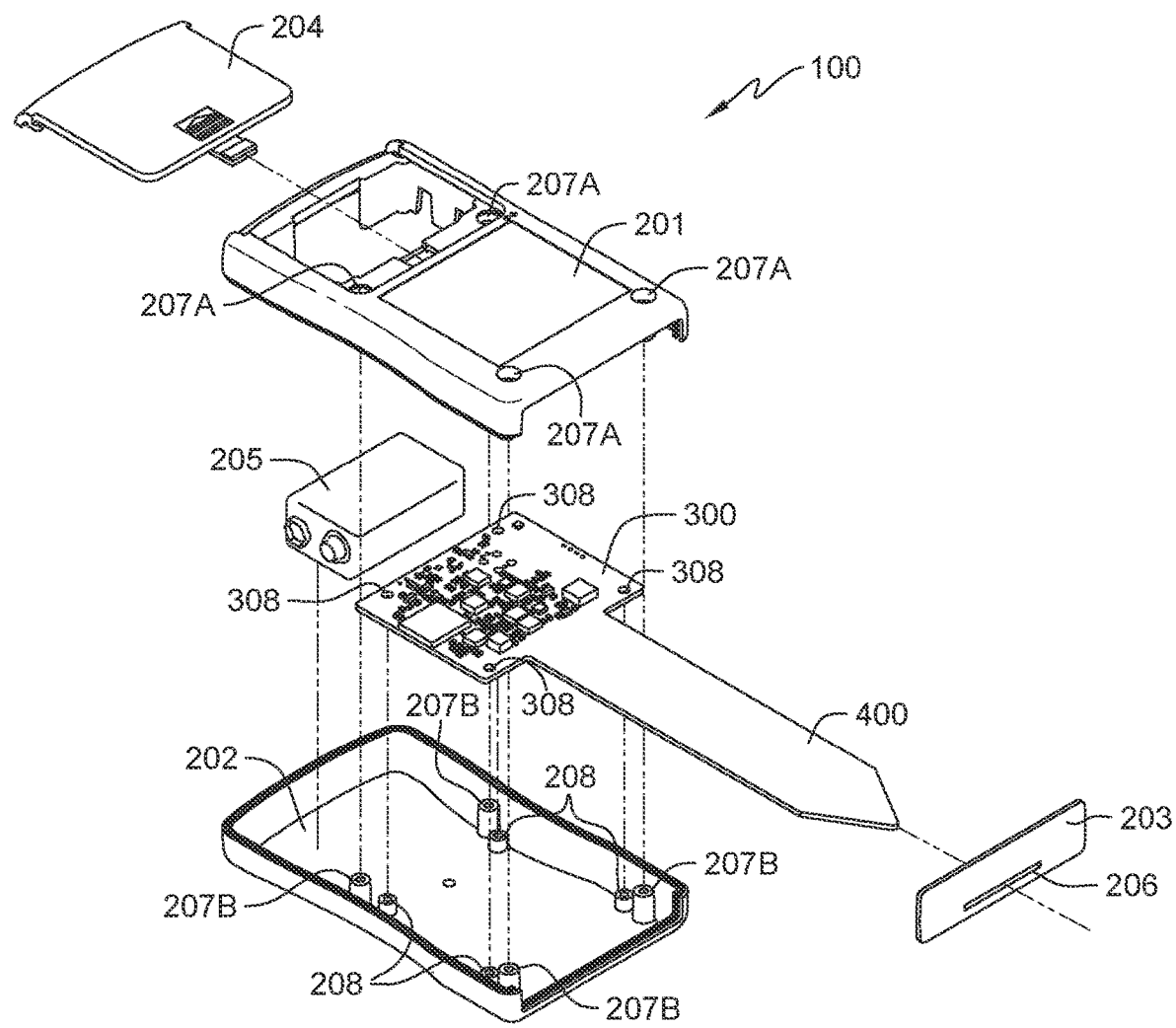
FIG. 4 depicts an exploded view of the soil sensor, according to an embodiment of the present invention.
Figure 5:
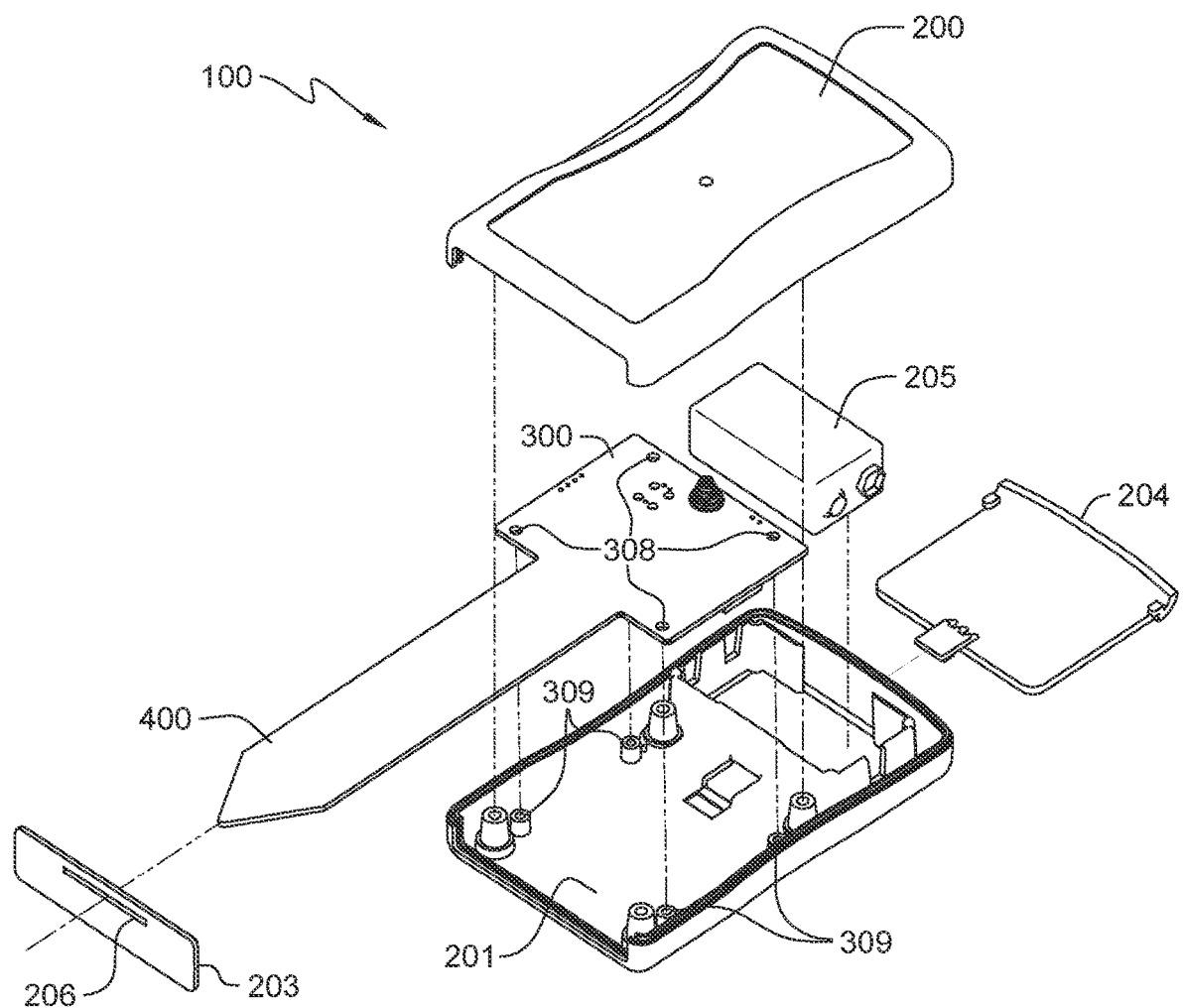
FIG. 5 depicts an exploded view of the soil sensor, according to an embodiment of the present invention.
Figure 7:
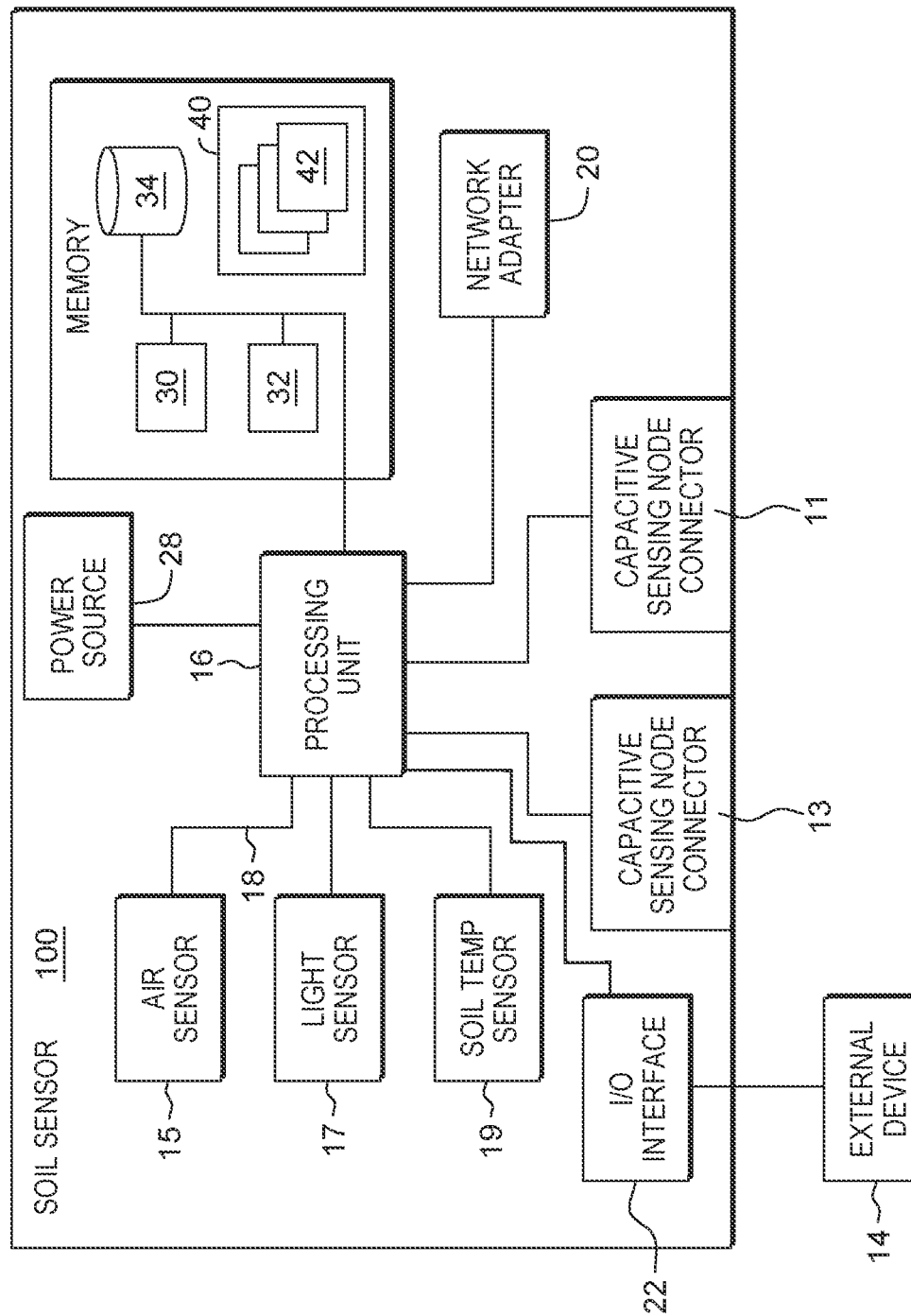
FIG. 7 depicts the soil sensor computing elements, according to an embodiment of the present invention.
Figure 7B:
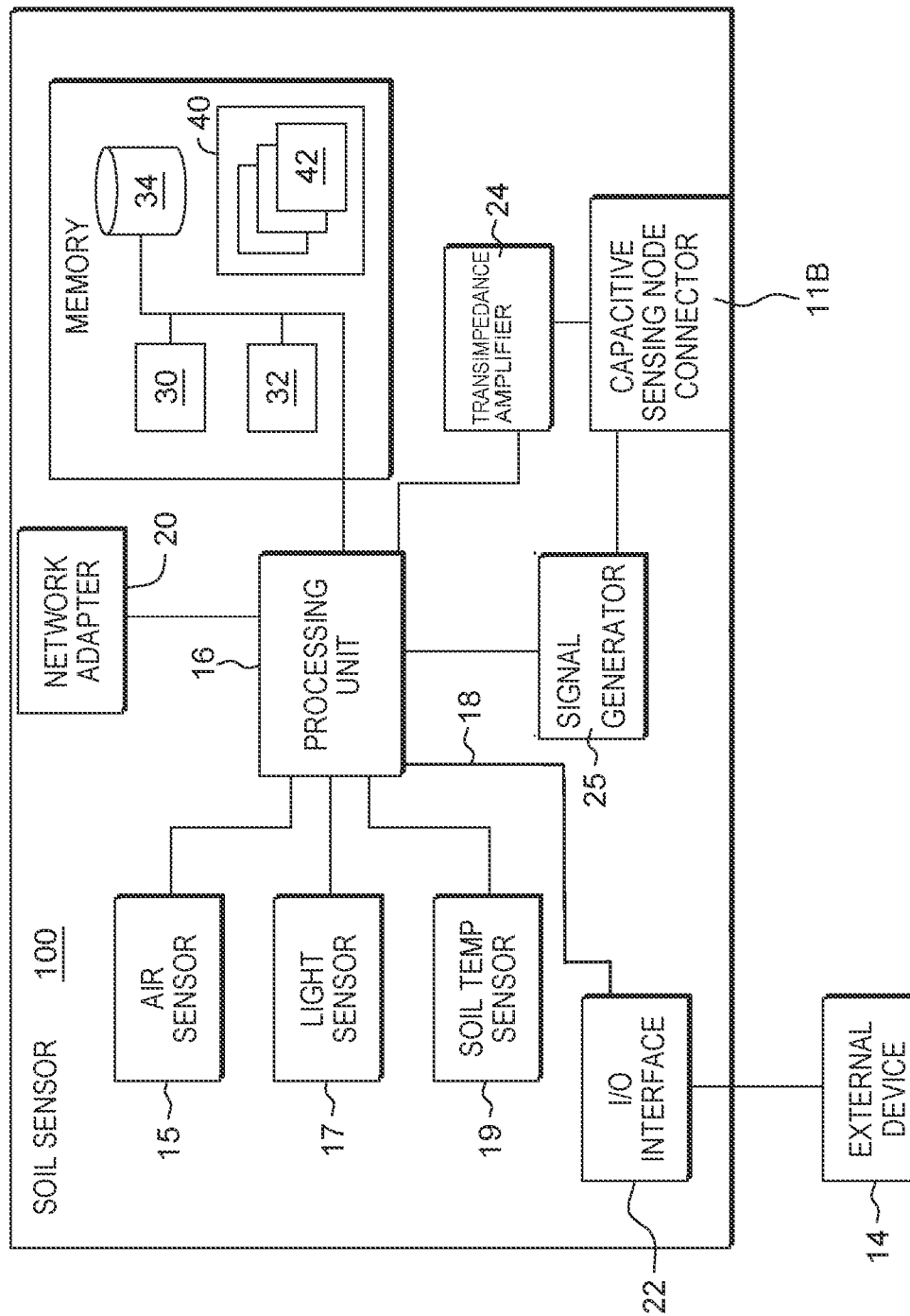
FIG. 7B depicts the soil sensor computing elements, according to an embodiment of the present invention.

As shown in FIG. 3B is an alternative design of the probe 400B, where one pair of capacitive sensing nodes 404 are present. In this embodiment, a signal generator is integrated into the system to allow for varying frequencies, so that a single capacitive sensing node 404 (or a pair as shown) can be used to collect data related to a variety of aspects of the soil (e.g., moisture, salinity, pH, etc.). As shown in FIG. 7B, a signal generator 25 and an transimpedance amplifier 24 are integrated into a system with a single capacitive sensing node connector 11B. The signal generator 25 can be integrated into the system to provide the ability to adjust the frequency of each capacitive sensing node, and an transimpedance amplifier 24 to converts the current of the capacitive sensing node(s) to a voltage measurement. With the ability to adjust the frequency of each capacitive sensing node, in some embodiments, a single capacitive sensing node is used. In these embodiments, the device performs the first test for moisture, salinity or other measurable value, at the desired frequency, and calculates a value for the specified measurable value. The signal generator 25 would then adjust the frequency for the second test for the other measurable value, and from the second set of collected data calculates the value. In these embodiments, where the probe 400 has only one type of capacitive sensing node, the capacitive sensing node is sized and shaped to provide the most accurate measurement of each desired value. In these embodiments, the signal generator 25 is capable of a wide frequency sweep from 5 kHz to 25 MHz at predetermined intervals. Through the collection of the data from the capacitive sensing nodes, the processing unit or an external computing device is able to calculate a variety of measurements from the soil, such as, but not limited to, salinity, moisture, PH, nitrogen, etc.

The measurement process is as follows. The oscillators are activated. Voltage measurements are taken of the output voltages of the oscillators prior to passing through the capacitive sensing nodes 401 and 402. Voltage measurements are taken of the electrical signal after passing through the capacitive sensing nodes 401 and 402 and a transimpedance amplifier. The activation of the oscillators and the respective voltage meters may happen in a predetermined order or sequence. The two voltage measurements are then used to calculate a voltage again across the capacitive sensing nodes 401 and 402 to calculate the moisture and salinity, respectively. The impedance of the measurement circuit is determined using these voltage gain values. Determining the capacitance of the capacitive sensing nodes 401 and 402 by injecting an AC voltage signal into the capacitive sensing nodes 401 and 402. The transimpedance amplifier is a component on the PCB that converts the current that flows through the capacitive sensing nodes 401 and 402 into a voltage. In some instances, this is done because the control unit is unable to directly measure current, so the transimpedance amplifier to output a voltage that is related to the current that is passing through the capacitive sensing nodes 401 and 402. The amplitude of this output voltage increases as the capacitance of the capacitive sensing nodes 401 and 402 increases. Thus, measuring the complex impedance of the measurement circuit which is a function of the capacitance, inductance, and frequency of the system. The inductance and frequency are controlled, the changes that are observed are primarily due to capacitance changes of the capacitive sensing nodes 401 and 402 due to moisture or salts.

Figure 6:
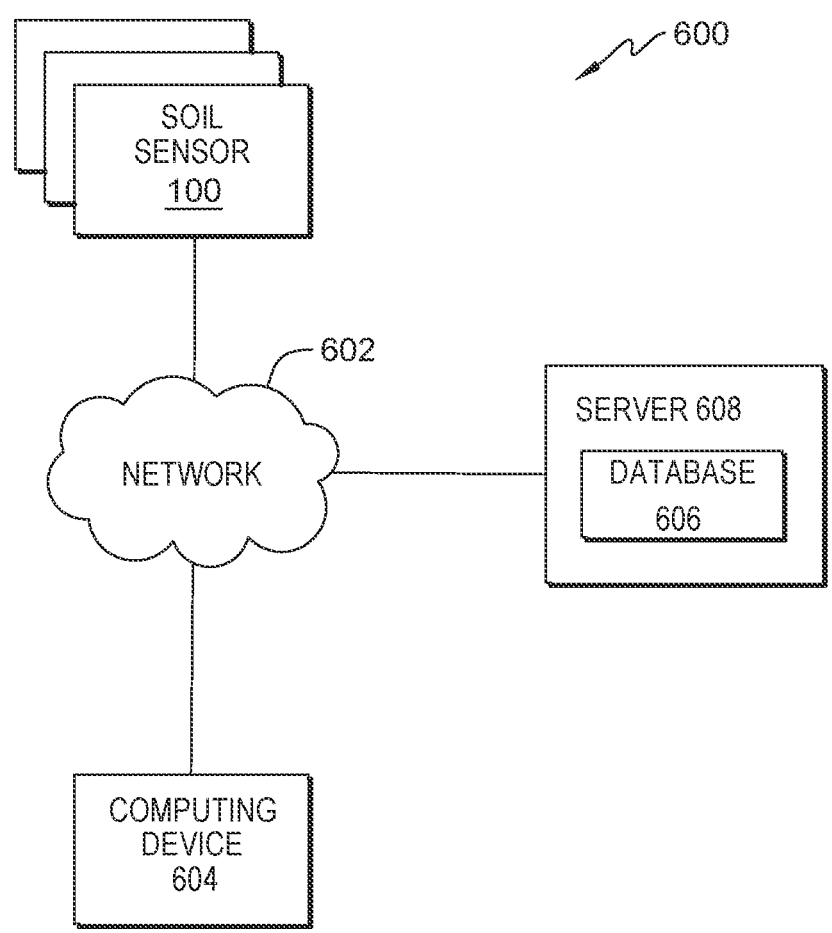
FIG. 6 depicts a computing environment, according to an embodiment of the present invention.

FIG. 6 depicts a block diagram of a computing environment 600 in accordance with one embodiment of the present invention. FIG. 1 provides an illustration of one embodiment and does not imply any limitations regarding the environment in which different embodiments maybe implemented. In the depicted embodiment, computing environment 600 includes network 602, soil sensor 100, computing device 604, and server 608. Computing environment 100 may include additional servers, computers, or other devices not shown.

Network 602 may be a local area network (LAN), a wide area network (WAN) such as the Internet, any combination thereof, or any combination of connections and protocols that can support communications between computing device 604, soil sensor 100, and server 608 in accordance with embodiments of the invention. Network 602 may include wired, wireless, or fiber optic connections.

Soil sensor 100 is as described above and provides for the collection of data from the soil and is able to wireless transmit the data to a computing device 604 or server 608. The soil sensor 100 measures soil moisture, salinity, temperature, humidity, and sun light values of a region of soil at its ground location and periodically transmits these values to the computing device 604. This data may be set to provide warnings or signals when the data sent is outside a set of predetermined values to alert a person to the changes in the soil or environment.

Computing device 604 may be a management server, a web server, or any other electronic device or computing system capable of processing program instructions and receiving and sending data. In some embodiments, computing device 604 may be a laptop computer, tablet computer, netbook computer, personal computer (PC), a desktop computer, or any programmable electronic device capable of communicating with soil sensor 100 and server 608 via network 602. In other embodiments, computing device 604 may represent a server computing system utilizing multiple computers as a server system, such as in a cloud computing environment. In another embodiment, computing device 604 represents a computing system utilizing clustered computers and components to act as a single pool of seamless resources.

Server 608 may be a management server, a web server, or any other electronic device or computing system capable of processing program instructions and receiving and sending data. In other embodiments server 608 may be a laptop computer, tablet computer, netbook computer, personal computer (PC), a desktop computer, or any programmable electronic device capable of communicating via network 602. In one embodiment, server 608 may be a server computing system utilizing multiple computers as a server system, such as in a cloud computing environment. In one embodiment, server 608 represents a computing system utilizing clustered computers and components to act as a single pool of seamless resources. In the depicted embodiment database 606 is located on server 608.

Database 606 may be a repository that may be written to and/or read by computing device 604 or soil sensor 100. Information gathered from the soil sensor 100 may be stored to database 606. In one embodiment, database 606 is a database management system (DBMS) used to allow the definition, creation, querying, update, and administration of a database(s).

Once the computing device 604 and the soil sensor 100 have been paired, the user can install the soil sensor 100 into the turf. To assist the user in finding an installation location with desirable wireless signal strength between the soil sensor 100 and computing device, the two devices can enter a wireless placement mode in which the button 209 changes colors to indicate when it is within range and outside of the range of the computing device. In the present embodiment, the button 209 is in communication with a metal spring with a capacitive touch feature. The processing unit performs a button scan every 100 ms to see if the capacitance of the node has increased due to the presence of a user's finger. Due to the button 209 being a capacitive touch button instead of a mechanical switch it does not require moving parts.

The soil sensor 100 circuit board 300 provides for the processing of the data collected by the various sensors and the capacitive sensing nodes 401 and 402 and either internally processing the data or sending the data via the wireless network. As shown in FIG. 7, the schematics of the circuit board 300 provide the necessary components to collect the data from the capacitive sensing nodes 401 and 402 and to process the data. Soil Sensor 100 as a computing node 10 is shown in the form of a general-purpose computing device. The components of the soil sensor 10 may include, but are not limited to, one or more processors or processing units 16, a system memory 28, an air sensing unit 15, a light sensing unit 17, a soil temperature sensing unit 19, a power source 28, a capacitive sensing node connector 13, and capacitive sensing node connector 11, and a bus 18 that couples various system components. In some embodiment, the capacitive sensing node connector 11 and 13 may be physical connectors for the probe 400 to connect the capacitive sensing nodes 401 and 402 to the processing unit 16. In other embodiments, the capacitive sensing node connectors 11 and 13 may be integrated into the circuit board 300 probe 400 unitary component as wires which connect the capacitive sensing nodes 401 and 402 to the processing unit 16. The processing unit 16 is capable of both receiving data as well as operating the commands to effectively measure the various properties of the soil.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

System memory 28 can include computer system readable media in the form of volatile memory, such as random-access memory (RAM) 30 and/or cache memory 32. computing device 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

The air sensing unit 15 collects the air temperature and humidity sensor to monitor ambient air conditions. There are two small apertures in the back plate 201 of the housing 200 that allow for ventilation. There is a piece of foam around the sensor and a cutout slot in the circuit board 300 to provide thermal isolation from the rest of the product interior.

The light sensing unit 17 is a phototransistor to roughly monitor light conditions. This is only used to determine light schedules and whether the lights are on or off. The phototransistor is concentric with the button 209 because it is currently the point of the housing with the most light coming through. Other embodiments could include improved light monitoring for PAR (photosynthetically active radiation) measurements.

The soil temperature sensing unit 19 measures the temperature of the soil. This is contained within the housing, but as close to the soil as possible. The soil temperature is reported to the user, but its purpose is also to better compensate the soil moisture and EC measurements. Other embodiments could include temperature monitoring on the blade of the sensor for more accurate readings.

Soil Sensor 100 may also communicate with one or more external devices 14 that enable a user to interact with soil sensor 100; and/or any devices (e.g., network card, modem, etc.) that enable soil sensor 100 to communicate with one or more other computing devices. The high frequency connection and the low frequency connection permit the connection of the probe 400 to the circuit board 300, wherein the connections electrically connect the respective capacitive sensing nodes 401 and 402 to the circuit board 300 and physically connect the probe 400 to the circuit board 300. In some embodiments, the probe 400 is removable and allows for the replacement of the probe 400. This provides a benefit of creating a variety of probes 400 with different capacitive sensing node designs to allow for the collection of various types of data. In the depicted embodiment, the circuit board 300 and the probe 400 are a single element, where the capacitive sensing nodes 401 and 402 are integrated into the circuitry of the circuit board 300. Such communication can occur via Input/Output (I/O) interfaces 22. Still yet, soil sensor 100 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to microcode, device drivers, redundant processing units, external disk drive arrays, RAID systems, tape drives, and data archival storage systems, etc.

While this invention has been described in conjunction with the specific embodiments outlined above, it is evident that many alternatives, modifications, and variations will be apparent to those skilled in the art. Accordingly, the preferred embodiments of the invention, as set forth above, are intended to be illustrative, not limiting. Various changes may be made without departing from the spirit and scope of this invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein that are believed as maybe being new, this understanding, as indicated by use of the term "present invention," is tentative and provisional and subject to change over the course of patent prosecution as relevant information is developed and as the claims are potentially amended.

The foregoing descriptions of various embodiments have been presented only for purposes of illustration and description. They are not intended to be exhaustive or to limit the present invention to the forms disclosed. Accordingly, many modifications and variations of the present invention are possible in light of the above teachings will be apparent to practitioners skilled in the art. Additionally, the above disclosure is not intended to limit the present invention. In the specification and claims the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

Although various representative embodiments of this invention have been described above with a certain degree of particularity, those skilled in the art could make numerous alterations to the disclosed embodiments without departing from the spirit or scope of the inventive subject matter set forth in the specification and claims. Joinder references (e.g., attached, adhered, joined) are to be construed broadly and may include intermediate members between a connection of elements and relative movement between elements. As such, joinder references do not necessarily infer that two elements are directly connected and in fixed relation to each other. Moreover, network connection references are to be construed broadly and may include intermediate members or devices between network connections of elements. As such, network connection references do not necessarily infer that two elements are in direct communication with each other. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements and/or substantial equivalents.

What is claimed is:

1. A sensor device comprising:
   a housing;
   a processing unit assembly disposed within the housing;
   a probe connected to the processing unit and substantially exposed;
   at least one sensing structure integrated into the probe and in electrical communication with the processing unit, wherein the at least one sensing structure provide information related to the moisture and salinity of soil, and the information is calculated by the processing unit based on data collected from the at least one sensing structures, and the at least one sensing structure comprising:
      high frequency sensing structures integrated along an edge of the probe, and
      low frequency sensing structures integrated along a center line of the probe of interlocking design,
      wherein a surface area of the low frequency sensing structures is greater than the high frequency sensing structure; and
   a signal generator in electrical communication with the processing unit and the at least one sensing structure.

2. The sensor device of claim 1, wherein, sensing structures are disposed within the probe, wherein the probe is of a predetermined thickness based on the sensing structures.

3. The sensor device of claim 1, further comprising; an air sensor contained with the housing.

4. The sensor device of claim 1, further comprising; a light sensor, contained within the housing, wherein the housing has an aperture positioned relative to the light sensor.

5. The sensor device of claim 1, further comprising; a temperature sensor, wherein the temperature sensor is contained within the housing and positioned distal to the probe.

6. The sensor device of claim 1, further comprising; a wireless connection module contained within the housing.

7. The sensor device of claim 1, further comprising; a power source contained within the housing and connected to the processing unit.

8. The sensor device of claim 1, wherein, the probe has a predetermined shape and profile based on the high frequency and low frequency sensing structures.

9. The sensor device of claim 1, wherein a gap is formed between the low frequency sensing structures and the gap is of a predetermined size.

10. The sensor device of claim 1, wherein the processing unit further includes at least one oscillator, wherein the at least on oscillator is in communication with the at least one sensing structure, and the at least one oscillator is able to generate predetermined frequency measurements to the at least one sensing structures.

11. A sensor device comprising:
    a housing;
    a processing unit assembly disposed within the housing, wherein the processing unit comprising a high frequency oscillator, a first voltage meter, a low frequency oscillator, a second voltage meter;
    a probe having a predetermined shape and profile attached to the processing unit and extending from the housing a predetermined distance;
    a first sensing unit integrated into the probe along an edge of the probe and in electrical communication with the high frequency oscillator and the first voltage meter; and
    a second sensing unit integrated into the probe along a centerline of the probe relative to the first sensing unit and in electrical communication with the low frequency oscillator and the second voltage meter,
    wherein a surface area of the first sensing unit is greater than the second sensing unit.

12. The sensor device of claim 11, wherein the first sensing unit, comprises, two members displaced along an exterior edge of the probe.

13. The sensor device of claim 11, wherein the processing unit controls the frequencies of the high and low frequency oscillators.

14. The sensor device of claim 11, wherein the frequencies of the high and low frequency oscillators are set at a predetermined value based on the first sensing unit and the second sensing unit physical properties.

15. The sensor device of claim 11, wherein the second sensing unit, comprises, two mating members of a predetermined profile and positioned distal to a centerline of the probe.

16. A sensor device comprising:
a housing;
a control module contained within the housing;
a probe extending from the housing; and
first sensing units integrated into the probe along an edge of the probe and in electrical communication with the control module; and
a second sensing unit integrated into the probe along a centerline of the probe and in electrical communication with the control module;
wherein the control module is able to measure the impedance of the first and second sensing units to calculate a moisture and salinity value, and a surface area of the first sensing unit is greater than the second sensing unit.

17. The sensor device of claim 16, wherein the control module measures a voltage gain across the first and second capacitive bridge to calculate a voltage gain across each sensing unit.

18. The sensor device of claim 16, wherein the control module comprises; a first oscillator and a first voltage meter and a first capacitive bridge connected to the first sensing unit and a second oscillator and a second voltage meter, and a second capacitive bridge connected to the second sensing unit, where the oscillators are adjusted based on a set of physical properties related to the first and second sensing units.

19. The sensor device of claim 16, wherein the control module comprises;
an air sensing circuit;
a temperature sensing circuit; and
a light sensing circuit.

* * * * *